US006939686B2

(12) United States Patent
Ling et al.

(10) Patent No.: US 6,939,686 B2
(45) Date of Patent: Sep. 6, 2005

(54) METHODOLOGY OF USING RAMAN IMAGING MICROSCOPY FOR EVALUATING DRUG ACTION WITHIN LIVING CELLS

(75) Inventors: Jian Ling, San Antonio, TX (US); Steven D. Weitman, San Antonio, TX (US); Michael A. Miller, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 221 days.

(21) Appl. No.: 10/750,603

(22) Filed: Dec. 31, 2003

(65) Prior Publication Data

US 2004/0157208 A1 Aug. 12, 2004

Related U.S. Application Data

(63) Continuation of application No. 09/804,774, filed on Mar. 13, 2001, now abandoned.
(60) Provisional application No. 60/189,123, filed on Mar. 14, 2000.

(51) Int. Cl.$^7$ .............................................. C12Q 1/02
(52) U.S. Cl. ............................. 435/29; 435/7; 436/173; 422/55; 356/301
(58) Field of Search ........................ 436/173; 356/301; 435/7; 422/55

(56) References Cited

U.S. PATENT DOCUMENTS

| | | | |
|---|---|---|---|
| 4,405,237 A | 9/1983 | Manuccia et al. | |
| 4,847,240 A | 7/1989 | Ryser et al. | |
| 5,580,750 A | 12/1996 | Doglia et al. | |
| 5,841,139 A | 11/1998 | Sostek et al. | |
| 5,902,732 A | 5/1999 | Hochman | |
| 5,965,352 A | 10/1999 | Stoughton et al. | |
| 6,002,471 A | 12/1999 | Quake | |
| 6,002,476 A | 12/1999 | Treado | |

OTHER PUBLICATIONS

Beljebbar et al, Raman and SERS microspectroscopy on living cells: a promising tool toward cellular drug response and medical diagnosis, Proceedings of SPEI–The Internationsl Society for Optical Engineering (1999), vol. 3608, (Biomedical Applications on Continued: Raman Spectroscopy), pp. 175–184.*
Whitley et al, Prodeedings of SPIE–The International Society for Optical Engineering (1998) vol. 3261, (Three–Dimensional Microscopy: Image Acquistion and Processing V), pp. 250–259.*
Otto et al, Applicantions iof micro–Raman imaging in biomedical research, Journal of Raman Spectroscopy (1997), vol. 28 (2 and 3), pp. 143–150.*
Paloley, J., The Handbook of Biological Confocal Microscopy, JMR Press 1989.

Manoharan R., Wang Y., Feld MS, "Histochemical Analysis of Biological Tissue Using Raman Spectroscopy",Spectrochimica Acta, Part A, 52, pp 210–249, 1996.
Ferraro Jr, et al, Introductory Raman Spectroscopy, Academic Press, Jul. 1994.
Brenan CJH, et al, "Volumetric Raman Spectral Imagaging with a Confocal Raman Microscope: Image Modalities & Applications" SPIE v 26ss, pp 130–139, 1996.
Kincade K, Raman Spectroscopy Enhances in vivo Diagnosis Laser Focus World, pp 83–91, Jul. 1998.
Turrell G, et al, Raman Microscopy–Developments & Applications, Academic Press 1996.
Buick RN, "Cellular Basis of Chemotherapy", Cancer Chemotherapy Handbook, Appletin & Lange Press 1994.
Jones RA, An Automated Technique for Deriving MTF from Edge Traces Photographic Science & Engineering VII (2), pp 102–106, 1967.
Blackman ES, Effects of Noise on the Determination of Photographic System Modulation Transfer Functions. Photographic Science & Engineering V12(5) pp 244–250, 1968.
Bovik, AC, "On Detecting Edges in Speckle Imagery", IEEE Trans. Acoust., Speech, Signal Processing, V36(10), pp 1618–1627, 1988.
Kondo K, et al, "Image Restoration by Weiner Filtering in the Presence of Signal–Dependent Noise", Appl. Opt., V16(0), pp 2254–2558, 1977.
Lim JS, Two–Dimensional Signal & Image Processing, Englewood Cliffs, Prentice Hall, pp 536–540, 1990.
Castleman KR, Digital Image Processing, Prentice Hall, Englewood Cliffs, New Jersey, pp 117, 1996.
Art J., "Photon Dectectors for Confocal Microscopy", Handbook of Biological Confocal Microscopy, Plenum Press, New York, pp 183–196, 1995.
Lee JS, Digital Image Enhancement and Noise Filtering by Use of Local Statistics, IEEE Trans. Pattern Anal. Mach. Intell, PAM 1–2, pp 165–168, 1980.
Perona P, Scale Space & Edge Detection Using Anistrophic Diffusion, IEE Trans. Pattern Anal. Mach. Intell, vol 12(7) pp 629–639, 1990.

(Continued)

Primary Examiner—Long V. Le
Assistant Examiner—Deborah A. Davis
(74) Attorney, Agent, or Firm—Gunn & Lee, PC

(57) ABSTRACT

A method of using Raman imaging microscopy to evaluate drug actions in living cells is disclosed. Specifically the invention describes the methods of using Raman imaging microscopy to detect drug uptake, distribution, binding, and metabolism in a single cell, and to study drug pharmacokinetics at the cellular level. The method involves measuring the Raman image of both the drug and the cell. Control images and post-treatment images of the cell were studied. Ratio images were calculated and the requisite information was obtained from a study of the intensity of the bright areas in the ratio images.

14 Claims, 7 Drawing Sheets

(4 of 7 Drawing Sheet(s) Filed in Color)

OTHER PUBLICATIONS

Sijtsema, Nmetal, Confocal Direct Imaging Raman Microscope: Design and Applications in Biology, Applied Spechoscopy, v52(3), pp 348–355, 1998.

Freeman TL, et al, Investigation of the Subcellular Localization of Zinc Phthalocyanines by Raman Mapping, Applied Spectroscopy, v52(10), pp 1257–1263, 1998.

S. Sharonov, I. Chourpa, H. Morjani, IL Nabiev and M. Manfait; Confocal spectral imaging analysis in studies of the spatial distribution of anitumour drugs within living cancer cells.

G.D. Sockalingum, A. Beljebbar, H. Morjani, J.F. Angiboust, M. Manfait; Characterization of Island Films as Surface–Enhanced Raman Spectroscopy Substrates for Detecting Low Antitumor Drug Concentrations at Single Cell Level.

* cited by examiner (a) (b)

METHODOLOGY OF USING RAMAN IMAGING MICROSCOPY FOR EVALUATING DRUG ACTION WITHIN LIVING CELLS

This is a continuation of U.S. patent application Ser. No. 09/804,774 filed on Mar. 13, 2001, now abandoned which claims benefit of 60/189,123 filed on Mar. 14, 2000.

BACKGROUND OF THE INVENTION

1. Field of the Invention

The present invention relates to a method of using an optical apparatus for drug development and evaluation. More specifically, the present invention provides a convenient and cost effective method to evaluate the action of a drug at the cellular level, including its uptake, distribution, binding characteristics, etc.

2. Background Information

The determination of drug action at the cellular level is a problem of great importance to drug evaluation and development. Recently, the implementation of rational drug design, combinatorial chemistry techniques, and high throughput screening have led to large numbers of new potential drugs. However, currently there is no cost effective way to understand the details of how these potential drugs work at the cellular level. This lack of methodology requires pharmaceutical companies to spend millions of dollars in animal and clinical studies to evaluate a candidate drug.

The most direct way of evaluating a drug, however, is its actions at the cellular level. For example, the efficacy of a drug is generally determined by the following drug-cell interactions: (1) cellular distribution of the drug, (2) cellular uptake of the drug, (3) binding characteristics of the drug, and (4) biochemical pathways of the drug.

Another major obstacle of drug efficacy is the resistance of some cells to a drug. The underlying molecular and cellular mechanisms of this resistance are not totally understood. However, a number of mechanisms appear to contribute to the resistance: (1) increased efficiency of DNA repair mechanism after the DNA has been damaged by the drug, (2) decreased cellular uptake or increased efflux of drugs, (3) increased levels of "target" enzymes or alterations in "target" enzymes, (4) decreased drug efficacy because of increased drug breakdown, and (5) alternative biochemical pathways.

In addition to the efficacy of the drug, the safety of a drug must also be evaluated at the cellular level. For example, to identify if a drug has allow toxicity to normal cells but high toxicity to tumor cells generally requires an understanding of the unique biochemical differences between normal and abnormal cells.

Using methods in molecular biology to study drug actions at the cellular level is difficult if only conventional optical microscopes are used. This is because biomolecules are generally transparent in visible light and are therefore indistinguishable under optical microscopes. A molecularly selective imaging microscope (sometimes called a chemical imaging microscope) is needed to differentiate between molecular targets.

Laser scanning fluorescent microscopy, as a chemical imaging technique, has been routinely used for in vitro sample analysis for many years. Molecular imaging is acquired by choosing a stain or fluorescing agent that selectively, chemically or physically, bonds to specific regions of the sample. Quantitative measurements of intensity in fluorescence can provide images that illustrate the distribution of fluorescent markers in cells. The distribution of these markers determines the distribution of specific antibodies, ligand affinities, or covalent bonds that are tagged by the markers. However, the fluorescent approach has several disadvantages and limitations: (1) the sample preparation procedure is complicated and time consuming, (2) the fluorescent markers used in the specimen may cause undesireable pharmacological or toxicological effects, (3) suitable markers are not available for all biomolecules, (4) the fundamental problems of fluorophore photon bleaching during measurement severely limit the use of fluorescence microscopy, and (5) the relatively short wavelength used in fluorescence microscopy can easily cause photo-damage to the specimen.

Infrared microscopy is another chemical imaging technique that can provide molecular-specific images. An image of a sample is obtained by imaging the transmitted infrared radiation. Molecular selectivity is obtained by tuning the wavelength to a vibrational energy level of a selected molecular type in the sample. Since infrared imaging is derived from a material's intrinsic vibrational energy level, no external markers, dyes, or labels are required to contract the infrared image. However the spatial resolution of the image is usually several times the wavelength of infrared radiation. This is usually 10–20 $\mu$m, which is too large to resolve structures at the cellular level. In addition, many samples of biological interest are opaque in the infrared due to the presence of water since vibrational modes with a high change of dipole moment have a large infrared sensitivity. Consequently, it is often difficult, and sometimes impossible to obtain images of many molecular groups of interest by infrared microscopy.

Raman spectroscopy, in contrast to infrared techniques, is a technique for determining the vibrational modes of a molecule that is based on the scattering of a photon from the molecule. The Raman spectrum, formed by a plurality of scattered frequencies shifted from the illumination wavelength, has a long history of being used to distinguish different molecules. The Raman spectrum of a particular substance depends on the structure (vibrational states and chemical bonds) of the molecules. Therefore, a Raman spectrum can uniquely identify a particular type of molecule by its unique combination of scattered frequencies (also referred to as Raman peaks or Raman modes).

Raman images, acquired at selected Raman modes using a tunable filter, can provide an overview of the spacial arrangement of a particular type of molecule within a heterogenous specimen. Like infrared imaging, Raman imaging requires no external markers, dyes, or labels as required in fluorescent imaging. However, Raman scattering is superior to infrared absorption or transmission measurements of biological systems in that water has little effect on the Raman spectrum and, therefore, interference by water in Raman are negligible compared to infrared imaging. This is expected since the sensitivity of the vibrational mode in the Raman spectrum is related to the change in polarizability of the vibration, rather than a high change in dipole moment which is characteristic of infrared.

In addition, near-infrared excitation of biological systems has a number of advantages in Raman imaging. With this excitation source, Raman imaging produces less laser-induced fluorescence and photo-thermal degradation, and allows better perspective depth into a living cell.

Unfortunately, the signal for a Raman spectrum is inherently weak compared to the strength of the fluorescent signals, and therefore, can be difficult to detect.

Consequently, Raman spectroscopy, especially Raman imaging, was not practical until the recent development of a number of new signal generation, processing and detection tools. Some examples are robust laser sources, holographic filters, and low-noise CCD (charge-coupled device) cameras. In addition, various Raman imaging techniques are being developed to enhance the Raman signal, for example, surface enhanced Raman imaging and coherent anti-stroke Raman imaging. The first commercial Raman imaging microscope became available in the early 1990s. Recently the Raman microscope has achieved resolution of 0.5 $\mu$m, and it is now feasible to obtain chemical imaging at the cellular level.

The present invention demonstrates that Raman imaging microscopy can be applied to the study of drug actions in a single cell. Specifically, the invention describes the methods of using Raman imaging microscopy to detect drug uptake, distribution, binding and metabolism in a single cell, and to study drug pharmacokinetics at the cellular level. Even though this application speaks to more conventional Raman imaging techniques, various enhanced Raman imaging techniques can be applied as well, including but not limited to, surface enhanced Raman imaging and anti-Stroke Raman imaging.

SUMMARY OF THE INVENTION

It is a primary object of the present invention to provide a method of using Raman imaging to estimate the cellular distribution of a drug.

Another objective of the present invention is to provide a method of using Raman imaging to detect the drug uptake within a cell.

Still another objective of the present invention is to provide a method of using Raman imaging to study the local binding and biochemical pathway of a drug.

Yet another objective of the present invention is to provide a method of using Raman imaging to study the cell resistance to a drug.

Another objective of the present invention is to provide a method of using Raman imaging to study drug pharmokinetics.

It is still another objective of the present invention to provide a method of using Raman imaging to study drug metabolism.

It is yet another objective of the present invention to provide a method which utilizes a petri dish coated with gold or other Raman inactive materials for Raman imaging of cells.

Still another objective of the present invention is to provide a numerical model for a Raman image that describes the physics of the imaging process and the degradation caused by a microscopic system.

Another objective of the present invention is to provide a method of Raman image restoration.

It is yet another objective of the present invention to provide a method of using ratio Raman imaging to indicate the drug action in a cell.

Still another objective of the present invention is to provide a method of using ratio Raman imaging to quantify local drug concentration.

Another objective of the present invention is to provide a convenient and cost effective method to evaluate the efficacy of drugs at the cellular level.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENT

FIGS. 1–7 represent the results obtained using Raman imaging microscopy in the study of interactions between the anticancer drug taxol and MDA435 breast cancer cells. While the present description speaks to this preferred embodiment, this technique could be used in the study of the interactions of any type of drug in any type of cell.

Figure 1:
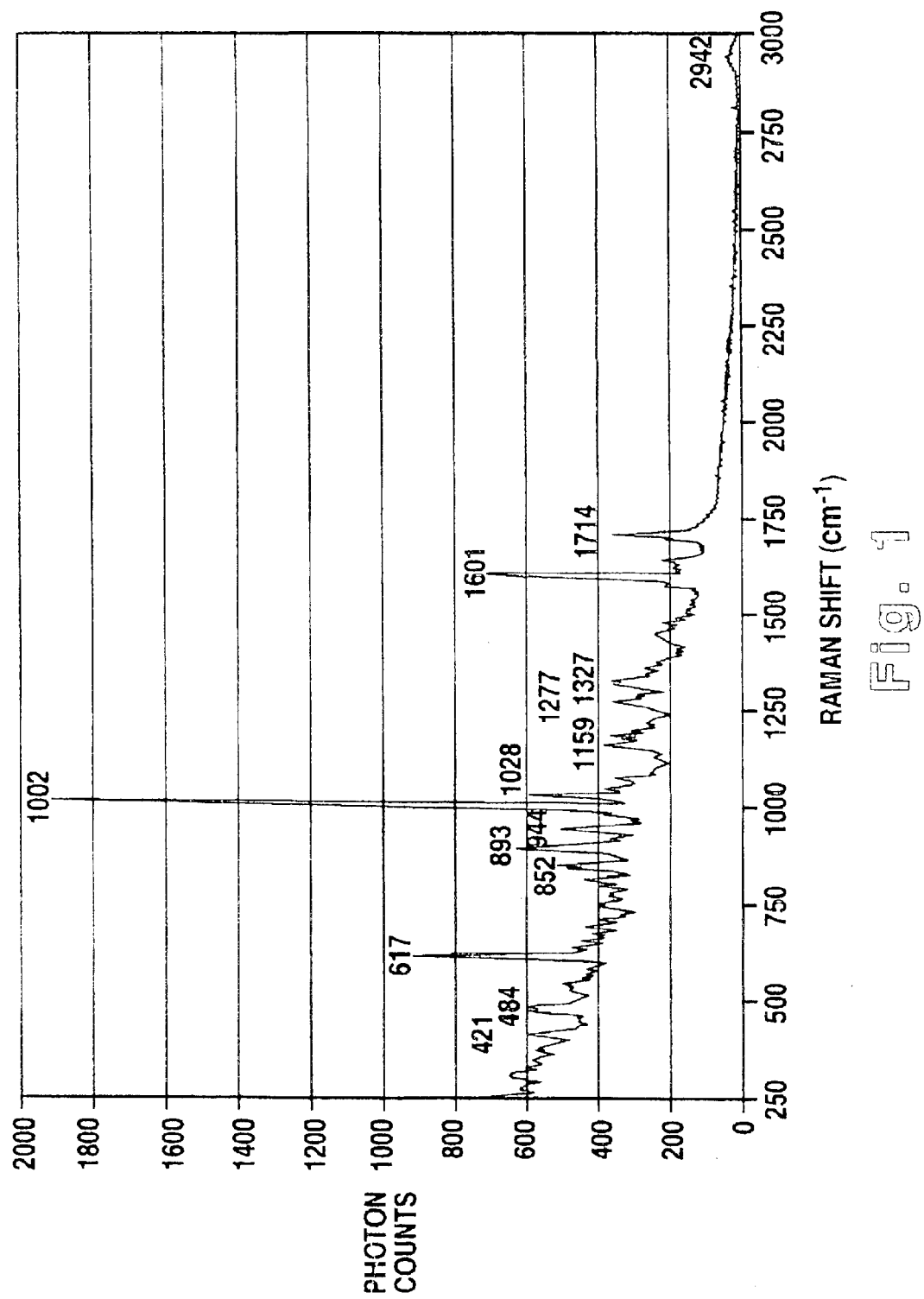
FIG. 1 is a Raman spectrum of the anti-cancer drug taxol.

Raman imaging of the cell-drug interactions consists of several steps. First, the Raman spectrum of the drug is measured. From the Raman spectrum, the locations and relative intensities of the Raman peaks (or Raman modes) is determined. The combination of the multiple Raman peaks and their relative intensities provides a unique fingerprint of the drug. In the preferred embodiment, the Raman spectrum of the anticancer drug taxol was measured as illustrated in FIG. 1. From the spectrum the most significant Raman mode is 1002 cm$^{-1}$.

Next, a Raman spectrum is obtained for the cells to determine their fingerprint and in order to ultimately distinguish the drug location from the cellular background. From the Raman spectrum of the cells, the locations and relative intensities of the Raman peaks is determined. These Raman peaks, however, may indicate Raman modes of different constituents of the cells.

Figure 2:
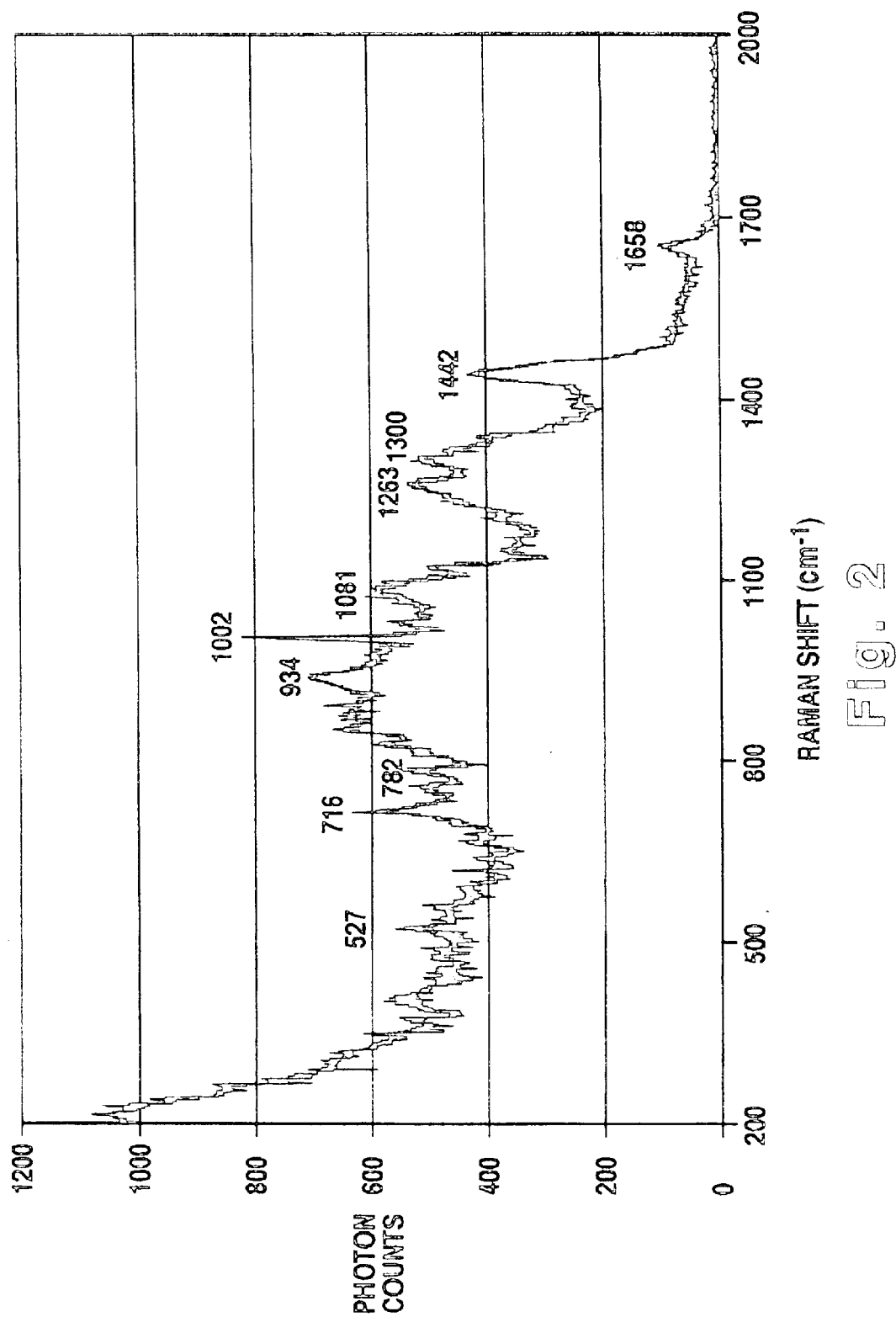
FIG. 2 is a Raman spectrum of cytoplasm in a MDA435 breast tumor cell.
Figure 3:
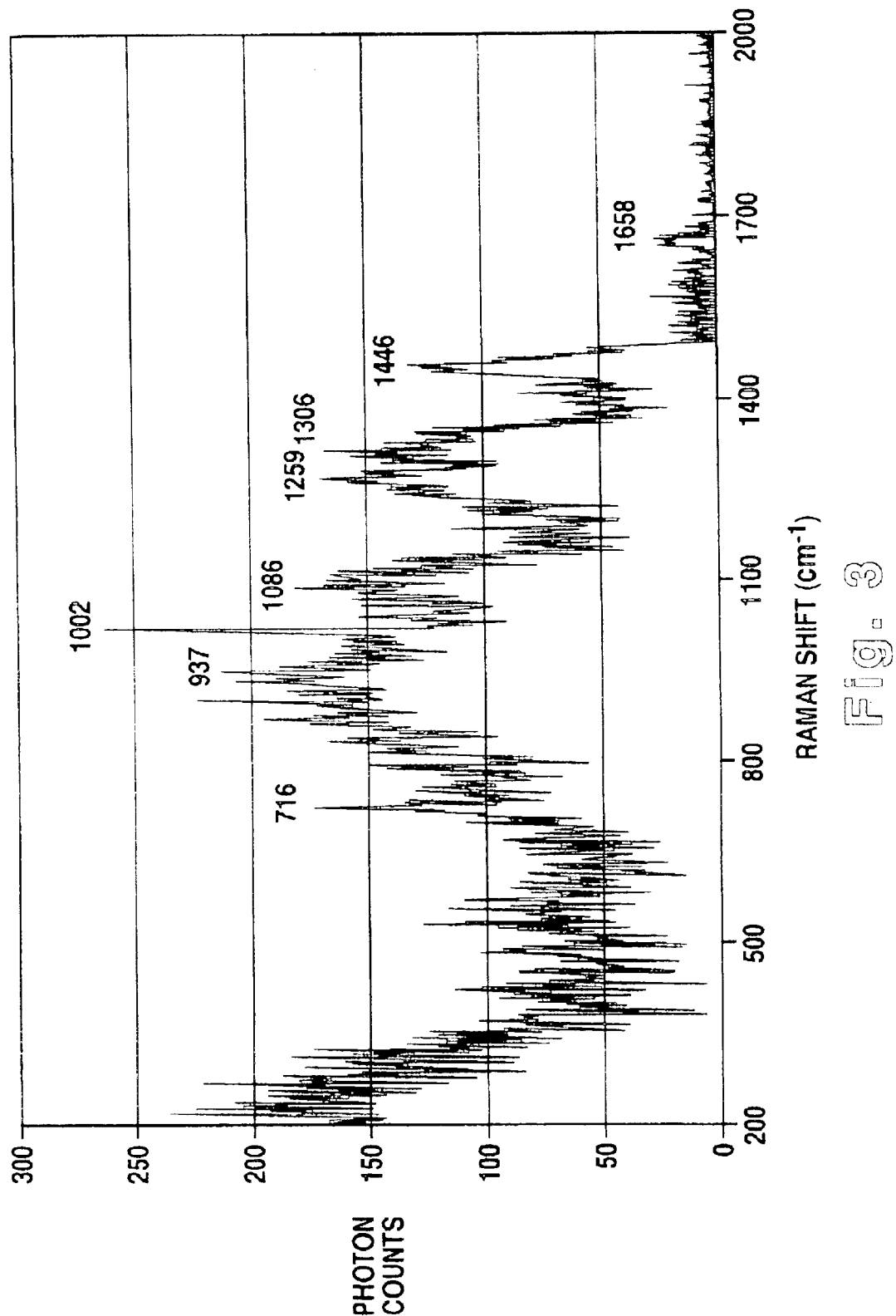
FIG. 3 is a Raman spectrum of the nucleus in a MDA435 breast tumor cell.

In the preferred embodiment the Raman signal of a breast tumor cell was studied and the Raman spectrum was measured. The tumor cell was cultured in a gold-coated (gold is a Raman inactive material) petri dish in order to prevent Raman signals coming from the petri dish during the measurement. The laser beam was focused in the cell cytoplasm and nucleus areas to determine if there was any difference in their spectra. Each measurement was 120 seconds long. FIGS. 2 and 3 illustrate the Raman spectra of the cytoplasm and nucleus of the breast tumor cell, respectively. The spectra are actually the combination of Raman signals from different cell constituents.

Subsequently, the cells are cultured in a petri dish coated with gold or other Raman inactive materials and allowed to adhere to the bottom of the petri dish. Raman images are acquired from a cell in phosphate buffered salt (PBS) at the Raman modes of the drug or at the cell constituent. The Raman modes are again determined. These obtained Raman images act as control images of the cell.

In the preferred embodiment approximately 500,000 breast cancer cells (MDA435) were plated on a gold-coated petri dish and allowed to stabilize for 24 hours prior to imaging. At Raman mode of 1002 cm$^{-1}$, direct Raman images (control images) were obtained from a cell in PBS solution.

Figure 4:
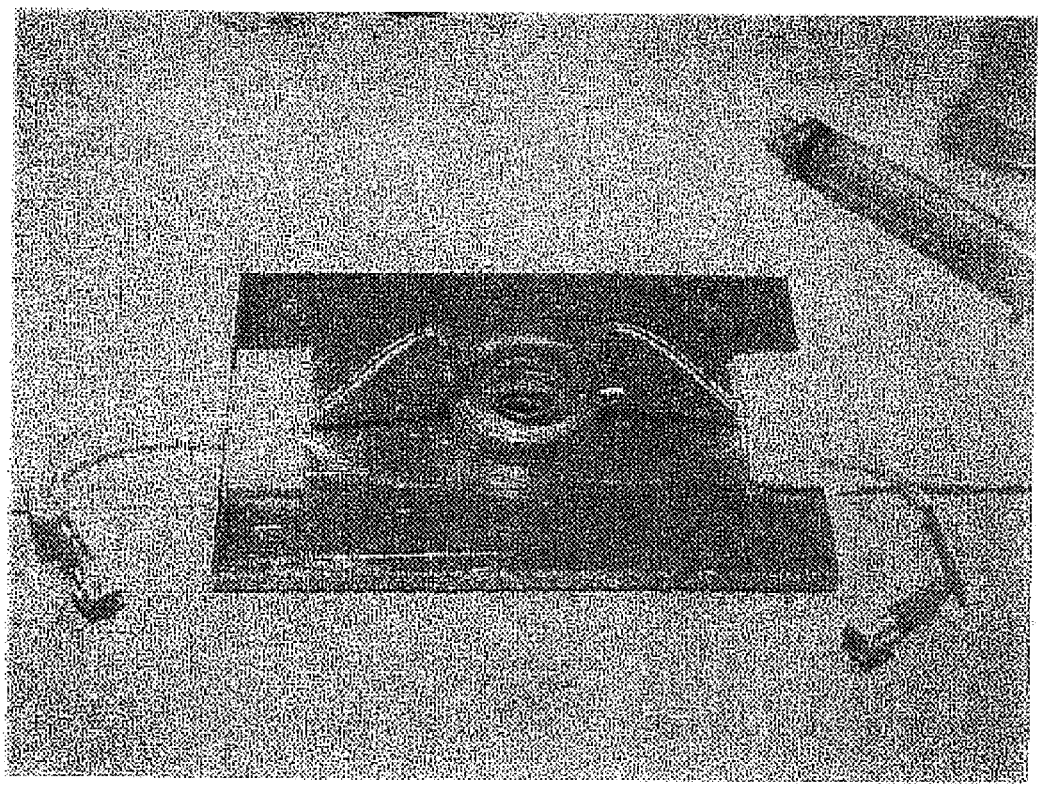
FIG. 4 is a drug delivery system for Raman imaging.
Figure 5:
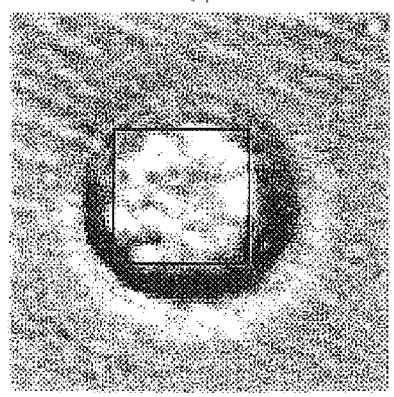
FIG. 5 is a Ratio Raman image (b) that illustrates the drug distribution (bright areas) within a breast tumor cell after treatment with 0.3 mg/ml taxol.
Figure 5:
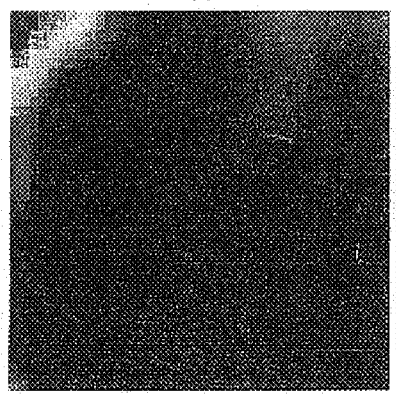
Figure 5:

Next, using the drug delivery system of FIG. 4, the PBS is replaced with the drug solution. The imaging position is maintained during this procedure. The cells are then exposed for a specific period of time. The drug solution is then withdrawn and the cells are reintroduced into the PBS solution. Raman images are again acquired at the same locations of the cell and at the Raman modes of the drug or the cell constituent. The obtained Raman images serve as post-treatment images of the cell.

In the preferred embodiment, using the drug delivery system illustrated in FIG. 4, 0.3 mg/ml taxol solution was carefully introduced into the petri dish to replace the PBS solution. After exposure to the taxol solution for one hour, the cells were reintroduced into the PBS solution. During the procedure of solution exchange, the imaging locations were kept unchanged. Raman images (post-treatment images) were taken again at the same locations and same Raman modes of the drug.

The acquired Raman images are then processed by smoothing noises, de-blurring, and removing the intensity contributed from the fluorescence. The processed post-treatment images were divided by the corresponding processed control images to create a ratio of images. The ratio of images indicate the changes of the cell after the drug treatment. With this procedure it is possible to obtain a stack of Raman images at various times and hence different depths of a cell separately. A three dimensional Raman image can be obtained by constructing the stack of two dimensional images.

If Raman images are taken at Raman modes of the drug, the ratio images indicate the drug accumulation and distribution within the cell. The relative drug uptake can be estimated from the intensity of the bright areas in the ratio images. Raman images taken at several Raman modes of a drug can be used to confirm the drug distribution. If Raman images are recorded for different cells, the ratio images indicate the drug distributions and uptakes for these cells, respectively. These images show the sensitivity of different cells to the drug. In general, the ratio images of drug sensitive cells have relatively high intensity or large bright areas compared to drug resistant cells.

If Raman images are obtained in the following cases: (1) a series of Raman images are taken at certain time intervals after cell exposure to a drug, (2) a series of Raman images are taken for the same type of cells treated with the same drug but with different exposure time, or (3) a series of Raman images are taken for the same type of cells treated with the same drug but with different concentration, the ratio images, indicating the changes of drug uptake and distribution along time and concentration, can be used to study the pharmokinetics of the drug.

If Raman images are taken at Raman modes of a specific cell constituent, the ratio images indicate the change in abundance of the constituent. This change will suggest the drug binding characteristics. The biochemical or metabolic pathway of the drug can also be derived from the information cell constituent changes.

Raman Image Processing

A difficulty with Raman imaging processing is that the recorded Raman images (both control and post-treatment images) suffer the following problems which make it difficult to identify the drug locations: (1) severe noise, (2) blurring by the microscope system, (3) non-uniform illumination effects caused by the laser system, and (4) mixed with fluorescent contribution.

In order to restore the degraded Raman images, a Raman image model was established based on the physics of Raman scattering as well as the Raman imaging system. The model is described in the following paragraphs.

Let us assume a laser beam illuminates a point at location (x,y) with an intensity of i(x,y) photons per second. The Raman scattering coefficient for the heterogeneous area is K(x,y). The fluorescent background is $K_o(x,y)$. Then the Raman signal s(x,y) can be modeled as:

$$s(x,y)=(K(x,y)+K_o(x,y))\cdot i(x,y)\cdot t,$$

where t is the exposure time. Usually the intensity of the illumination i(x,y) is dependent on the location of x and y. This hetereogeneity of the illumination causes the non-uniform illumination effect on the recorded images.

If we assume the images formation system is a linear and time invariant system with a point spread function (PSF) h(x,y), then the recorded image g(x,y) can be represented as:

$$g(x,y)=h(x,y)*s(x,y)+n(x,y)$$

where n(x,y) is the additive noise during image recording and * is the linear convolution operator. The Raman signal s(x,y) was blurred by the PSF of the microscopic system because of the limited resolution and further degraded by the additive noise.

The purpose of the Raman image processing is to determine the Raman scattering coefficient K(x,y) of the imaging area from the recorded image g(x,y). In order to determine K(x,y), we (1) reduced the noise n(x,y) from the image g(x,y), (2) compensated for the point-spread function h(x,y), and (3) eliminated the non-uniform illumination i(x,y) and subtracted the fluorescent background $K_o(x,y)$ from the image.

Before developing Raman imaging processing algorithms, the following tasks were completed. First, the PSF of the Raman microscopic system was estimated by measuring the Raman image of an edge target. From the estimated PSF, the resolution of the microscopic system is about 0.7 μm. Second, the noise model was established by measuring Raman images of a uniform surface. The additive noise is signal-dependent, Gaussian, and white. And third, synthetic Raman images were generated based on the model.

Using the synthetic images, an anistropic diffusion filter was developed which effectively reduced the signal dependent Gaussian noise without blurring the edges of the Raman signals. After noise smoothing, a Wiener filter was developed using the estimated PSF. The Wiener filter de-blurred the Raman images and restored the Raman signal s(x,y) from the recorded image g(x,y).

The restored Raman signal still contained the non-uniform illumination effect and fluorescent contribution, illustrated as follows:

$$s(x,y)=K(x,y)\cdot i(x,y)\cdot t+K_o(x,y)\cdot i(x,y)\cdot t.$$

From the Raman spectra illustrated in FIGS. 1–3, Raman peaks are riding on a broadband baseline that is contributed from the fluorescence. For Raman images, the equivalent fluorescent baseline is the background intensity $K_o(x,y)\cdot i(x,y)\cdot t$. The fluorescent background in the post-treatment Raman image usually had lower intensity than the fluorescent background in the control Raman image due to the accumulation of fluorescent bleaching. This often caused the total intensity in post-treatment image to be lower than that of the control image, which makes comparison of the two images meaningless (since we assume the drug areas in the post-treatment image should have higher Raman energy or be brighter than that in the control image). If the minimum value of the Raman image is subtracted from every point on the image, most parts of the fluorescent background are eliminated (assume most of the fluorescent background is contributed by water, which is fully distributed in a cell and surrounding solution). After the subtraction, the control Raman image and post-treatment Raman image of the cell become:

$$s(x,y)=K(x,y) \cdot i(x,y) \cdot t, \text{ and } s'(x,y)=K'(x,y) \cdot i(x,y) \cdot t,$$

respectively. Taking the ratio of the two images s(x,y) and s'(x,y) produces the ratio image $$\frac{s'(x, y)}{s(x, y)}$$

which cancels out the non-uniform illumination.

$$\frac{s'(x, y)}{s(x, y)} \quad \frac{K'(x, y)}{K(x, y)}$$

The ratio image indicates the concentration change of the target molecules in the cell after drug treatment. In this case the target molecule is taxol. Taxol is believed to be located in the areas where s'(x,y) is greater than 1.

Results and Discussion

The ratio image in FIG. 5(b) illustrates that the taxol is located on the top (left corner and right corner) of the image. The closer to the membrane, the higher the taxol concentration. This indicates that taxol entered the tumor cell from the top membrane and gradually penetrated into the center of the cell. More drugs entered the top-left membrane than the top-right membrane. The breast tumor cell was exposed to 0.3 mg/ml taxol solution for one hour in this experiment.

Figure 6:
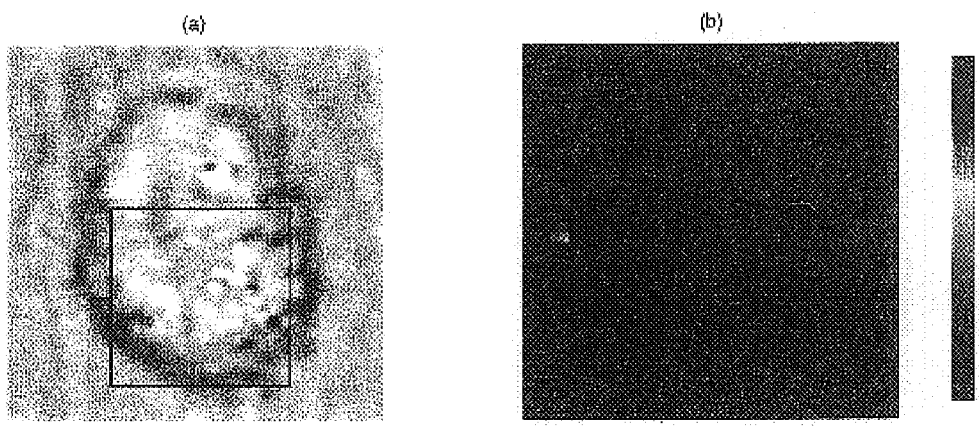
FIG. 6 is a Ratio Raman image (b) that illustrates there is no drug distribution within a breast tumor cell after treatment with 0.3 mg/ml diluent-only solution.

FIG. 6 illustrates the Raman image of a cell treated with taxol-diluent-only solution. The solution was prepared the same as the taxol solution, but without taxol. The cell was exposed to the diluent for one hour, the same period of time as the experiment with the taxol solution. FIG. 6(b) indicates there is no drug distribution in the cell (one bright spot on the image is most likely the noise).

Figure 7:
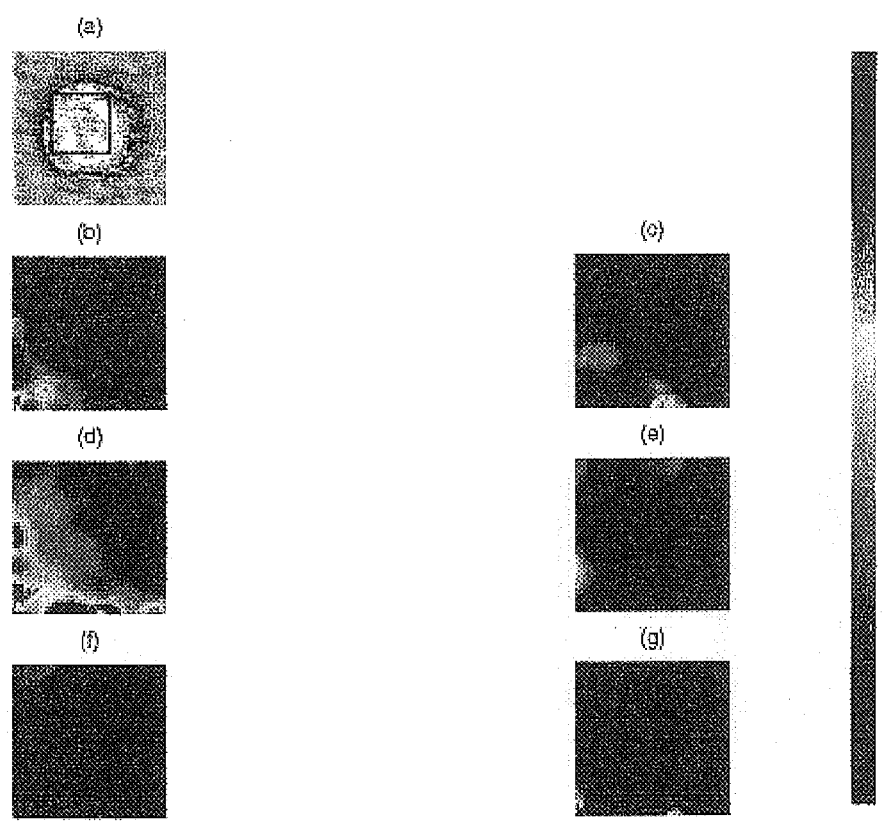
FIG. 7 illustrates Ratio Raman images (b–g) that show drug distribution at different depths of a breast tumor cell after treatment with 0.3 mg/ml taxol.

FIG. 7 illustrates a stack of Raman images at different depths of a breast tumor cell. The tumor cell was also treated with 0.3 mg/ml taxol solution for one hour. The drugs entered the cell from various locations at different layers: some from the top, some from the left, and some from the bottom. More drug entered the cell from the middle layer (Z=6 $\mu$m) (The height of the cell is about 10 to 12 $\mu$m). From this set of 2-D images, a 3-D drug distribution image can be constructed for the cell. The volume, concentration, and the relative uptake of the drug can be estimated.

Instrumentation

For the study, a Renishaw Model 2000 Raman microscopic system (Gloucestershire, UK, 1993) was used. This system is capable of taking Raman spectra, scanning dot-by-dot Raman images, and performing fast direct Raman imaging with an expanded laser beam. A 30-mw diode laser at 780 nm was used as the excitation source. The system can achieve the spectral resolution of 1 cm$^{-1}$ for spectral measurement. For direct imaging, the tunable filter has a bandwidth of 10–20 cm$^{-1}$.

The Raman system was put in a dark room to eliminate ambient light during imaging and also to provide better isolation from noise and dust. In addition, the system was stabilized on a vibration-controlled table—the Vibraplane Air Suspension System (Kinetic System, Inc., Boston, U.S.A.). This setup provides an ideal imaging environment.

A 60× Olympus water immersion, high infrared (IR) transmission objective (1-UM571 LUMPLFL 60× W/IR, Olympus, Japan) was used to obtain living cells cultured in aqueous solution. This lens is specially designed for the use of near infrared wavelengths. The transmission coefficient of the lens at 780 nm excitation wavelength is 71%.

This lens has a numerical aperture (NA) of 0.90. The calculated diffraction-limited resolution of the lens is about 0.53 $\mu$m. By considering the magnification of the microscope and the pixel size of the CCD camera, the microscope system can achieve spatial resolution of 0.7 $\mu$m.

This lens has a depth of field (DOF) of 1.2 $\mu$m. DOF is the depth through which the objective can be focused without any appreciable change in the sharpness of the image. In other words, all the features within the DOF will be sharply in focus in the recorded image. From this parameter we also understand that the axial resolution of the microscope is about 1.5–2 $\mu$m.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

What is claimed is:

1. A method of using Raman imaging microscopy for evaluating drug action within living cells comprising the steps of:

first measuring a Raman spectrum of said drug to determine a pretreatment fingerprint of said drug;

second measuring a first direct Raman image of said living cells at a predetermined wavelength on said Raman spectrum in order to determine a pretreatment background of said living cells;

treating a culture of said living cells with said drug to obtain treated living cells;

next measuring a second direct Raman image of said treated living cells at said predetermined wavelength on said Raman spectrum to obtain post-treatment images of said living cells;

processing said post-treatment images and pretreatment backgrounds to obtain processed post-treatment images and processed pretreatment backgrounds to evaluate said drug action within said living cells; and dividing said processed post-treatment images by said processed pretreatment backgrounds according to the formula s'(x,y)/s(x,y)=K'(x,y)/K(x,y), where s'(x,y) is said processed post-treatment image, s(x,y) is said processed pretreatment background, K'(x,y) is the Raman scattering coefficient for said processed post-treatment image, and K(x,y) is the Raman scattering coefficient for said processed pretreatment background, wherein said dividing step is used to obtain a ratio of images which indicate the changes of said living cells after said treating whereby said changes are used to determine said drug action.

2. The method of using Raman imaging microscopy for evaluating drug action within living cells of claim 1 wherein said ratio of images is obtained for various times to determine different depths within said living cells.

3. The method of using Raman imaging microscopy for evaluating drug action within living cells of claim 2 further comprising the step of stacking said ratio of images to obtain a three dimensional Raman image.

4. The method of using Raman imaging microscopy for evaluating drug action within living cells of claim 3 wherein said processing step comprises determining the Raman scattering coefficient of an imaging area from a recorded image for said post-treatment images and said pretreatment fingerprints.

5. The method of using Raman imaging microscopy for evaluating drug action within living cells of claim 4 wherein said processing step further comprises determining said Raman scattering coefficient by compensating for any point spread function.

6. The method of using Raman imaging microscopy for evaluating drug action within living cells of claim 2 further comprising the step of plating said living cells on a dish coated with Raman inactive material to prevent Raman signals coming from said dish during said measuring steps.

7. The method of using Raman imaging microscopy for evaluating drug action within living cells of claim 6 wherein said treating step occurs for a specific period of time.

8. The method of using Raman imaging microscopy for evaluating drug action within living cells of claim 7 wherein said measuring steps utilize a system having a Raman microscope with a 30 mw diode laser at 780 nm as the excitation source.

9. The method of using Raman imaging microscopy for evaluating drug action within living cells of claim 8 wherein said system is stabilized on a vibration controlled table.

10. The method of using Raman imaging microscopy for evaluating drug action within living cells of claim 9 wherein said living cells are obtained with a water immersion, high infrared transmission objective.

11. The method of using Raman imaging microscopy for evaluating drug action within living cells of claim 10 wherein said transmission objective has a transmission coefficient of the lens at 780 nm excitation wavelength of 71%.

12. The method of using Raman imaging microscopy for evaluating drug action within living cells of claim 11 wherein said lens has a numerical aperture of 0.90.

13. The method of using Raman imaging microscopy for evaluating drug action within living cells of claim 1 wherein said evaluation of said drug action within said living cells comprises one or more of the following process steps:

a) estimating the cellular uptake of said drug;

b) detecting said drug distribution within said living cell;

c) determining the local binding and biochemical pathway of said drug;

d) determining the cellular resistance of said living cells to said drug;

e) analyzing the pharmacokinetics of said drug; and f) determining the metabolism of said drug.

14. The method of using Raman imaging microscopy for evaluating drug action within living cells of claim 1 wherein said ratio of images is used to quantify the local concentration of said drug within said living cells.

* * * * *